United States Patent [19]
Lorenz et al.

[11] 3,980,783
[45] Sept. 14, 1976

[54] O-ALKYL-S-[3-OXO-TRIAZOLO-(4,3-α-PYRIDIN(2)YL-METHYL]-(THIONO)THIOL-PHOSPHORIC(PHOSPHONIC) ACID ESTERS AND ESTER-AMIDES

[75] Inventors: Walter Lorenz, Wuppertal; Ingeborg Hammann, Cologne; Bernhard Homeyer, Opladen, all of Germany

[73] Assignee: Bayer Aktiengesellschaft, Leverkusen, Germany

[22] Filed: May 9, 1975

[21] Appl. No.: 576,073

[30] Foreign Application Priority Data

May 21, 1974 Germany............................ 2424571

[52] U.S. Cl........................... 424/263; 260/294.8 K; 260/294.8 C
[51] Int. Cl.² ................... C07D 213/44; A01N 9/22
[58] Field of Search................ 260/294.8 C; 424/263

[56] References Cited
UNITED STATES PATENTS 3,919,244  11/1975  Kristinsson et al.......... 260/294.8 C

*Primary Examiner*—Alan L. Rotman
*Attorney, Agent, or Firm*—Burgess, Dinklage & Sprung

[57] ABSTRACT

O-Alkyl-S-[3-oxo-triazolo-(4,3-α)-pyridin(2)ylmethyl]-(thiono)thiol-phosphoric(phosphonic) acid esters and ester-amides of the formula

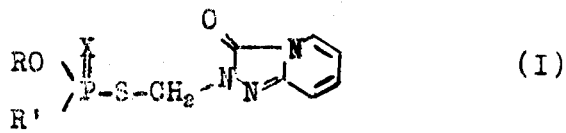

in which
R is alkyl with 1 to 6 carbon atoms,
R' is amino, or alkyl, alkoxy or alkylamino each with 1 to 6 carbon atoms, and
x is oxygen or sulfur, which possess insecticidal, acaricidal and fungicidal properties.

10 Claims, No Drawings

O-ALKYL-S-[3-OXO-TRIAZOLO-(4,3-α)-PYRIDIN-(2)YL-METHYL]-(THIONO)THIOL-PHOSPHORIC(PHOSPHONIC) ACID ESTERS AND ESTER-AMIDES

The present invention relates to and has for its objects the provision of particular new O-alkyl-S-[3-oxo-triazolo-(4,3-α)-pyridin(2)ylmethyl]-(thiono)thiol-phosphoric(phosphonic acid esters and ester-amides, i.e. O,O-dialkyl-S-[3-oxo-triazolo-(4,3-α)-pyridin(-2)ylmethyl]-thiolphosphoric acid esters, O-alkyl-S-[3-oxo-triazolo-(4,3-α)-pyridin(2)ylmethyl]-alkanethiolphosphonic acid esters, O-alkyl-S-[3-oxo-triazolo-(4,3-α)-pyridin(2)ylmethyl]-phosphoric acid ester-amides, and their thiono counterparts, which possess insecticidal, acaricidal and fungicidal properties, active compositions in the form of mixtures of such compounds with solid and liquid dispersible carrier vehicles, and methods for producing such compounds and for using such compounds in a new way especially for combating pests, e.g. insects, acarids and fungi, with other and further objects becoming apparent from a study of the within specification and accompanying examples.

It is known from Patent Nos. 2,758,115 and 2,791,599 that benzotriazinedithiophosphoric acid esters, for example O,O-dimethyl- (Compound A) and O,O-diethyl-S-[4-oxo-benzotriazin(3)yl-methyl]-thionothiolphosphoric acid ester (Compound B), and O,O-dimethyl-S-(ethylthioethyl)-thiolphosphoric acid ester (Compound C) possess insecticidal and acaricidal properties.

The present invention provides S-triazolopyridinemethyl-(thiono)thiol-phosphoric(phosphonic) acid esters and ester-amides of the formula

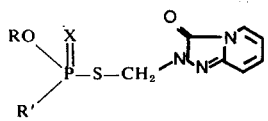   (I)

in which
R is alkyl with 1 to 6 carbon atoms,
R' is amino, or alkyl, alkoxy or alkylamino each with 1 to 6 carbon atoms, and
X is oxygen or sulfur.

Preferably, R is straight-chain or branched alkyl with 1 to 4 carbon atoms, and R' is straight-chain or branched alkyl or alkoxy with 1 to 4 carbon atoms, or monoalkylamino or dialkylamino each with 1 to 3 carbon atoms, or amino.

Surprisingly, the S-triazolopyridinemethyl-(thiono)-thiol-phosphoric(phosphonic) acid esters and ester-amides according to the invention show a better insecticidal, soil-insecticidal and acaricidal action than the previously known compounds of analogous structure and of the same type of action. The compounds according to the invention thus represent a genuine enrichment of the art.

The invention also provides a process for the production of a S-triazolopyridinemetnyl-(thiono)-thiol-phosphoric(phosphonic) acid ester or ester-amide of the formula (I) in which a (thiono)-thiol-phosphoric(phosphonic) acid ester or ester-amide of the formula

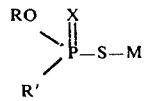   (II)

in which
R, R' and X have the abovementioned meanings, and
M is hydrogen or one equivalent of an alkali metal, alkaline earth metal or ammonium,
is reacted with a 2-halomethyl-3-oxo-triazolopyridine of the formula

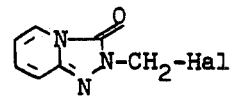   (III)

in which
Hal is halogen, optionally in the presence of an acid acceptor and optionally in the presence of a solvent.

If, for example, the potassium salt of O-ethyl-N-ethyl-thionothiolphosphoric acid ester-amide and 2-chloromethyl-3-oxo-triazolo-(4,3-α)-pyridine are used as starting materials, the course of the reaction can be represented by the following formula scheme:

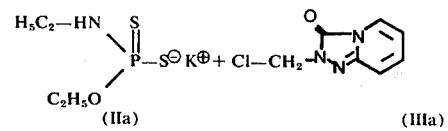

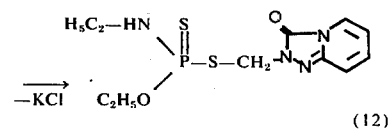

The (thiono)thiol-phosphoric(phosphonic) acid esters and ester-amides (II) are known from the literature and can be prepared according to generally customary methods, as can the 2-halomethyl-3-oxo-triazolo-(4,3-α)-pyridine, which can be prepared from the known 3-hydroxy-triazolo-(4,3-α)-pyridine [Chemische Berichte 99 (1966), pages 2,593 – 2,597] by reaction with formaldehyde, via the hydroxymethyl compound and halogenation thereof, for example with thionyl chloride.

The following may be mentioned individually as examples of the above: the salts of O,O-dimethyl-, O,O-diethyl-, O,O-di-n-propyl-, O,O-di-iso-propyl-, O,O-di-n-butyl-, O,O-di-iso-butyl-, O,O-di-sec.-butyl-, O,O-di-tert.-butyl-, O-ethyl-O-n-propyl-, O-ethyl-O-iso-propyl-, O-n-butyl-O-ethyl-, O-ethyl-O-sec.-butyl- and O-ethyl-O-methyl- thiolphosphoric acid diester and the corresponding thiono analogues, as well as O-methyl-, O-ethyl-, O-n-propyl-, O-iso-propyl-, O-n-butyl, O-sec.-butyl-, O-iso-butyl- and O-tert.-butyl- methane- or -ethane-, -n-propane-, -iso-propane-, -n-butane-, -iso-butane-, -sec.-butane- and -tert.-butane- thiolphosphonic acid ester and the corresponding thiono analogues, and also O-methyl-N-methyl-, O-ethyl-N-methyl-, O-n-propyl-N-methyl-, O-iso-propyl-N-methyl-, O-n-butyl-N-methyl-, O-sec.-butyl-N-methyl-, O-methyl-N-ethyl-, O-ethyl-N-ethyl-, O-n-propyl-N-ethyl-, O-iso-propyl-N-ethyl-, O-n-butyl-N-ethyl-, O-sec.-butyl-N-ethyl-, O-methyl-N-n-propyl-, O-ethyl-N-n-propyl-, O-n-propyl-N-n-propyl-, O-iso-propyl-N-ethyl- and O-tert.- butyl-N-ethyl-thiolphosphoric acid ester-amide, the corresponding dialkylamino compounds, the free amides and, in each case, the corresponding thiono analogues.

The reaction of the invention is preferably carried out in the presence of a solvent, which term includes a mere diluent. Practically all inert organic solvents can be used for this purpose. These include, in particular, aliphatic and aromatic optionally chlorinated hydrocarbons, for example, benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

All customary acid-binding agents can be employed as acid acceptors. Alkali metal carbonates and alkali metal alcoholates, such as sodium carbonate and potassium carbonate, sodium methylate and ethylate and potassium methylate and ethylate have proved particularly successful, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at 0° to 120°C, preferably at 15 to 50°C.

The reaction is in general allowed to take place under normal pressure.

To carry out the process, the salt-like component is in general employed in an excess of 15 to 20% and the reactants, in most cases in one of the solvents mentioned, are heated for one to several hours at the temperatures mentioned. The mixture is then worked up in the usual manner, for example by filtering, distilling off the solvent, dissolving the residue in water and salting it out, or by pouring the reaction mixture into water and filtering off the oil which separates out and solidifies.

Some of the new compounds are obtained in the form of oils which in most cases cannot be distilled without decomposition but may be freed from the last volatile constituents by so-called "slight distillation", that is to say by prolonged heating under reduced pressure to moderately elevated temperatures, and may be purified in this way. They are characterized by the refractive index. Some of the compounds are obtained in a crystalline form of sharp melting point.

As already mentioned, the S-triazolo-pyridinemethyl(thiono)thiol-phosphoric(phosphonic) acid esters and esteramides according to the invention are distinguished by an oustanding insecticidal (including soil-insecticidal) and acaricidal activity. They are active against leaf pests and pests of the soil, hygiene pests and pests of stored products. They couple a low phytotoxicity with a good action against both sucking and biting insects and mites and in addition some compounds also exhibit a fungicidal action, for example against *Pellicularia sasakii*.

For this reason, the compounds according to the invention can be employed successfully as pesticides in plant protection and in the hygiene field and the field of protection of stored products.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (Hyponomeuta padella), the Mediterranean flour moth (Ephestia kuhniella) and greater wax moth (Galleria mellonella).

Also to be classed with the biting insects are beetles (Coleoptera), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (Dermestes frischi), the khapra beetle (Trogoderma granarium), the flour beetle (Tribolium castaneum), the northern corn billbug (Calandra or *Sitophilus zeamais*), the drugstore beetle (Stegobium paniceum), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattela germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*) the northern house mosquito (*Culex pipiens*) and the malaria mosquito (*Anopheles stephensi*).

With the mites (Acari) there are classed, in particular, the spider mites (Tetranychidae) such as the twospotted spider mite (*Tetranychus urticae*) and the European red mite (*Paratetranychus pilosus* = *Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against hygiene pests and pests of stored products, particularly flies and mosquitoes, the process products are also distinguished by an outstanding residual activity on wood and clay, as well as a good stability to alkaki on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides, and fungicides, or nematocides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, acarids and fungi, and more particularly methods of combating insects and acarids, which comprises applying to at least one of correspondingly (a) such insects, (b) such acarids, (c) such fungi, and (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

Example 1 Laphygma test Solvent: 3 parts by weight of acetone Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cotton leaves (*Gossypium hirsutum*) were sprayed with the preparation of the active compound until dew-moist and were then infested with caterpillars of the owlet moth (*Laphygma exigua*).

After the specified periods of time, the destruction in % was determined. 100% means that all caterpillars had been killed while 0% indicates that no caterpillars had been killed.

The active compounds, the concentrations of the active compounds, the evaluation times and the results can be seen from the following Table 1.

Table 1

Laphygma test

| Active compounds | | Active compound concentration in % by weight | Degree of destruction in % after 3 days |
|---|---|---|---|
| $CH_3O\!\!\diagdown\!\!\underset{\displaystyle CH_3O\!\!\diagup}{\overset{\displaystyle O}{\|}}P\!-\!S\!-\!CH_2\!-\!CH_2\!-\!SC_2H_5$ | (C) | 0.1<br>0.01 | 80<br>0 |
| $(CH_3O)_2\overset{\displaystyle S}{\underset{\|}{P}}\!-\!S\!-\!CH_2\!-\!N\!\!\diagdown\!\!\underset{N}{\overset{O}{\diagup}}\!\!\diagdown\!\!\diagup$ | (2) | 0.1<br>0.01 | 100<br>100 |
| $\underset{\displaystyle CH_3\!\!\diagup}{\overset{\displaystyle C_2H_5O\!\!\diagdown}{}}\overset{\displaystyle S}{\underset{\|}{P}}\!-\!S\!-\!CH_2\!-\!N\!\!\diagdown\!\!\underset{N}{\overset{O}{\diagup}}\!\!\diagdown\!\!\diagup$ | (6) | 0.1<br>0.01 | 100<br>70 |
| $(CH_3O)_2\overset{\displaystyle O}{\underset{\|}{P}}\!-\!S\!-\!CH_2\!-\!N\!\!\diagdown\!\!\underset{N}{\overset{O}{\diagup}}\!\!\diagdown\!\!\diagup$ | (8) | 0.1<br>0.01 | 100<br>100 |
| $(C_2H_5O)_2\overset{\displaystyle O}{\underset{\|}{P}}\!-\!S\!-\!CH_2\!-\!N\!\!\diagdown\!\!\underset{N}{\overset{O}{\diagup}}\!\!\diagdown\!\!\diagup$ | (9) | 0.1<br>0.01 | 100<br>80 |
| $\underset{\displaystyle iso\text{-}C_3H_7O\!\!\diagup}{\overset{\displaystyle CH_3O\!\!\diagdown}{}}\overset{\displaystyle O}{\underset{\|}{P}}\!-\!S\!-\!CH_2\!-\!N\!\!\diagdown\!\!\underset{N}{\overset{O}{\diagup}}\!\!\diagdown\!\!\diagup$ | (11) | 0.1<br>0.01 | 100<br>90 |

Example 2 Doralis test (systemic action) Solvent: 3 parts by weight of acetone Emulsifier: 1 part by weight of alkylaryl polyglycol ether To produce a suitable preparation of active compound, 1 part by weight of the active compound was mixed with the stated amount of solvent and the stated amount of emulsifier, and the concentrate was diluted with water to the desired concentration.

Bean plants (*Vicia faba*) which had been heavily infested with the bean aphid (*Doralis fabae*) were watered with the preparation of the active compound so that the preparation penetrated into the soil without wetting the leaves of the bean plants. The active compound was taken up from the soil by the bean plants and thus passed to the infested leaves.

After the specified periods of time, the degree of destruction was determined as a percentage. 100% means that all the aphids were killed; 0% means that none of the aphids were killed.

The active compounds, the concentrations of the active compounds, the evaluation times and the results can be seen from the following Table 2:

Table 2

Doralis test (systemic action)

| Active compounds | | Active compound concentration in % by weight | Degree of destruction in % after 4 days |
|---|---|---|---|
| 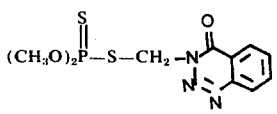 | [A] | 0.1 | 0 |
| 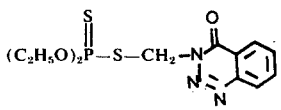 | [B] | 0.1 | 0 |
| 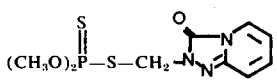 | (2) | 0.1 | 100 |
| 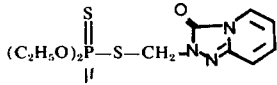 | (5) | 0.1 | 100 |
| 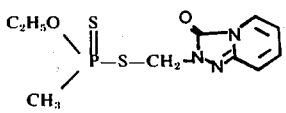 | (6) | 0.1 | 100 |
| 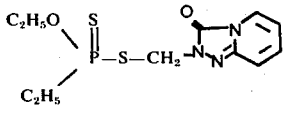 | (7) | 0.1 | 100 |
| 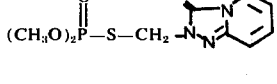 | (8) | 0.1 | 100 |
| 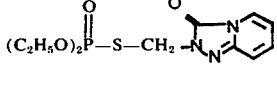 | (9) | 0.1 | 100 |
| 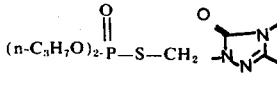 | (1) | 0.1 | 100 |
| 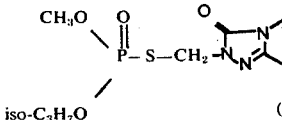 | (11) | 0.1 | 100 |

Example 3 Tetranychus test (resistant) Solvent: 3 parts by weight of acetone Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the common or two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following Table 3:

emulsifier was added and the concentrate was diluted with water to the desired concentration.

The preparation of active compound was intimately mixed with soil. The concentration of the active compound in the preparation was of practically no importance; only the amount by weight of active compound per unit volume of soil, which is given in ppm (= mg/l) was decisive. The soil was filled into pots and the pots were left to stand at room temperature.

Table 3

Tetranychus test (resistant)

| Active compounds | | Active compound concentration in % by weight | Degree of destruction in % after 2 days |
|---|---|---|---|
| 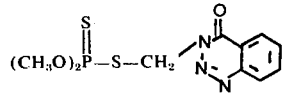 | [A] | 0.1<br>0.01 | 60<br>0 |
| 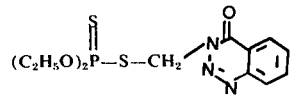 | [B] | 0.1<br>0.01 | 50<br>0 |
| 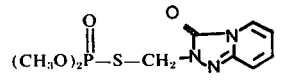 | (8) | 0.1<br>0.01 | 100<br>60 |

Example 4 Critical concentration test/soil insects Test insect: Tenebrio molitor Solvent: 3 parts by weight of acetone Emulsifier: 1 part by weight of alkylaryl polyglycol ether To produce a suitable preparation of active compound, 1 part by weight of active compound was mixed with the stated amount of solvent, the stated amount of After 24 hours, the test insects were introduced into the treated soil and after a further 2 to 7 days the degree of effectiveness of the active compound was determined in % by counting the dead and live test insects. The degree of effectiveness was 100% if all test insects had been killed and was 0% if just as many test insects were still alive as in the case of the untreated control.

The active compounds, the amounts used and the results can be seen from Table 4 which follows:

Table 4

Soil insecticides Tenebrio molitor

| Active compound | | Active compound concentration in ppm | Degree of destruction in % |
|---|---|---|---|
| 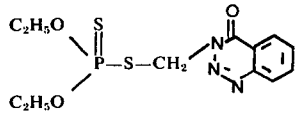 | (B) | 10 | 0 |
| 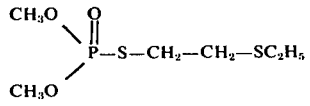 | (C) | 10 | 0 |
| 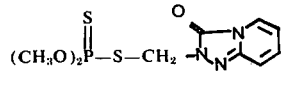 | (2) | 10 | 100 |
| 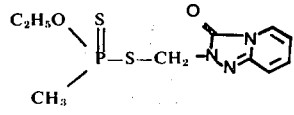 | (6) | 10 | 100 |

Table 4-continued

| | Soil insecticides Tenebrio molitor | |
|---|---|---|
| Active compound | Active compound concentration in ppm | Degree of destruction in % |

| Active compound | concentration in ppm | Degree of destruction in % |
|---|---|---|
| $C_2H_5O\underset{C_2H_5}{\overset{S}{\diagdown}}\!\!\overset{\parallel}{P}\!\!-\!\!S\!-\!CH_2\!-\!\!\begin{array}{c}\text{triazolopyridinone}\end{array}$ (7) | 10 | 100 |
| $(CH_3O)_2\overset{O}{\overset{\parallel}{P}}\!-\!S\!-\!CH_2\!-\!\!\begin{array}{c}\text{triazolopyridinone}\end{array}$ (8) | 10 | 100 |
| $(C_2H_5O)_2\overset{O}{\overset{\parallel}{P}}\!-\!S\!-\!CH_2\!-\!\!\begin{array}{c}\text{triazolopyridinone}\end{array}$ (9) | 10 | 100 |

Example 5 a. The 2-halomethyl-3-oxo-triazolo-(4,3-α)-pyridine used as the starting materials was prepared as follows:

i.
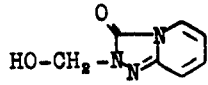

A mixture of 108 g (0.8 mole) of 3-hydroxytriazolo-(4,3-α)-pyridine [ Chemische Berichte 99 (1966), pages 2,593 - 2,597] of melting point 235°C and 756 ml of formaldehyde was warmed to 90°C on a water bath. Initially, the mixture was a paste which thickened up, while at 90°C it was almost a clear solution. It was left to stand for 1 hour and then cooled, and the precipitate which separated out was filtered off. After washing and drying the precipitate, 108 g (82% of theory) of 2-hydroxymethyl-3-oxo-triazolo- (4,3-α)-pyridine were obtained in the form of fine, pale yellow crystals of melting point 209°C (decomposition).

ii.
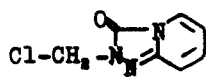 (IIIa)

143 g (1.2 moles) of thionyl chloride were added to a mixture of 165 g (1 mole) of the compound obtained as described under (i), in 1 liter of methylene chloride and 3 ml of dimethylformamide, a slight rise in temperature being noted. After approximately 1 hour, a clear solution was obtained which crystallized slowly. The reaction mixture was poured into 1 liter of water and neutralized with sodium bicarbonate, and the phases were separated. The organic phase was dried, the solvent was distilled off and the residue was crystallized. 160 g (87% of theory) of 2-chloromethyl-3-oxo-triazolo-(4,3-α)-pyridine were obtained in the form of fine yellow crystals of melting point 129°C.

b.
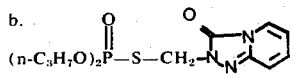 (1)

55 g (0.3 mole) of 2-chloromethyl-3-oxo-triazole-(4,3-α)-pyridine were added to 77.5 g (0.36 mole) of the ammonium salt of 0,0-di-n-propyl-thiolphosphoric acid diester in 300 ml of acetone, whereupon a slight temperature rise occurred. The reaction mixture was stirred at room temperature overnight, then stirred for a further hour at 40°–50°C, cooled and filtered. The solvent was distilled off and the oil which remained was taken up in toluene. The organic phase was washed with water and sodium bicarbonate solution until neutral and was dried and the solvent was distilled off. 73 g (70.5% of theory) of 0,0-di-n-propyl-S-[3-oxo-triazolo-(4,3-α)-pyridin(2)ylmethyl]-thiolphosphoric acid ester were obtained as an orange-colored oil of refractive index $n_D^{21}$: 1.5466.

Example 6

 (2)

55 g (0.3 mole) of 2-chloromethyl-3-oxo-triazolo-(4,3-α)-pyridine were added to 63 g (0.36 mole) of the ammonium salt of 0,0-dimethyl-thiono-thiolphosphoric acid diester in 250 ml of acetone, whereupon a slight temperature rise occurred. After the reaction mixture had been stirred overnight at room temperature, it was poured into water. The oil which separated out solidified and was filtered off, dried and recrystallized from a benzene-ligroin mixture. 64 g (70% of theory) of 0,0-dimethyl-S-[3-oxo-triazole-(4,3-α)-pyridin(2)-ylmethyl]- thionothiophosphoric acid ester of melting point 107°C were obtained.

Example 7

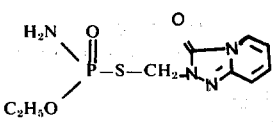 (3)

37 g (0.2 mole) of 2-chloromethyl-3-oxo-triazolo-pryidine were added to 48 g (0.24 mole) of sodium salt of 0-ethylthiolphosphoric acid ester-amide in 300 ml of acetone, the reaction mixture was stirred for 2 hours at 50°C and filtered while warm, and the solvent was distilled off. The residue was dissolved in water, salted out with sodium sulfate and extracted by shaking with methylene chloride. The organic phase was dried, the solvent was distilled off and the oil which remained was triturated with ether. The oil crystallized throughout and was recrystallized from acetonitrile. 35 g (60.5% of theory) of 0-ethyl-S-[3-oxo-triazolopyridin(2)ylmethyl]-thiolphosphoric acid ester-amide of melting point 142°C were obtained.

Example 8

The following compounds of the formula

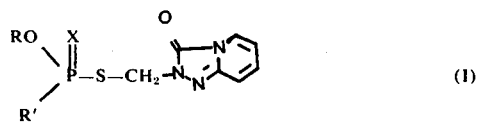

in which R, R' and X are identified in the following Table, were prepared analogously to Examples 6 - 8.

| Compound No. | R | R' | X | Physical data (refractive index, melting point) |
|---|---|---|---|---|
| 4 | —$C_2H_5$ | —$N(CH_3)_2$ | O | $n_D^{21}$: 1.5740 |
| 5 | —$C_2H_5$ | —$OC_2H_5$ | S | 71°C |
| 6 | —$C_2H_5$ | —$CH_3$ | S | 67°C |
| 7 | —$C_2H_5$ | —$C_2H_5$ | S | $n_D^{21}$: 1.6050 |
| 8 | —$CH_3$ | —$OCH_3$ | O | 99°C |
| 9 | —$C_2H_5$ | —$OC_2H_5$ | O | $n_D^{21}$: 1.5575 |
| 10 | —$C_3H_7$-iso | —$OC_3H_7$-iso | O | 85°C |
| 11 | —$CH_3$ | —$OC_3H_7$-iso | O | $n_D^{21}$: 1.5474 |

It will be appreciated that the instant specification and examples are set forth by way of illustration and not limitation, and that various modifications and changes may be made without departing from the spirit and scope of the present invention.

What is claimed is:

1. An 0-alkyl-S-[3-oxo-triazolo-(4,3-α)-pyridin-(2)ylmethyl]-(thiono)thiol-phosphoric(phosphonic) acid ester or ester-amide of the formula

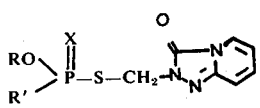

in which
R is alkyl with 1 to 6 carbon atoms,
R' is alkyl or alkoxy each with 1 to 6 carbon atoms, and
X is oxygen or sulfur.

2. A compound according to claim 1 in which R is alkyl with 1 to 4 carbon atoms and R' is alkyl or alkoxy each with 1 to 4 carbon atoms.

3. A compound according to claim 1 wherein such compound is 0,0-dimethyl-S-[3-oxo-triazolo-(4,3-α)-pyridin-(2)ylmethyl]-thionothiolphosphoric acid ester of the formula

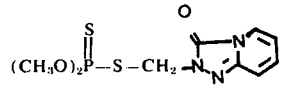

4. A compound according to claim 1 wherein such compound is 0-ethyl-S-[3-oxo-triazolo-(4,3-α)-pyridin(2) ylmethyl]-methanethionothiolphosphonic acid ester of the formula

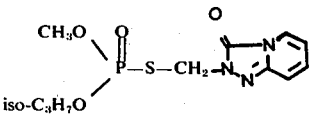

5. A compound according to claim 1 wherein such compound is 0,0-dimethyl-S-[3-oxo-triazolo-(4,3-α)-pyridin-(2)ylmethyl]-thiolphosphoric acid ester of the formula

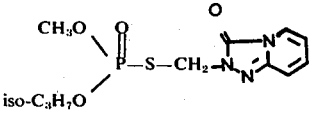

6. A compound according to claim 1 wherein such compound is 0,0-diethyl -S-[3-oxo-triazolo-(4,3-α)-pyridin-(2)ylmethyl]-thiolphosphoric acid ester of the formula

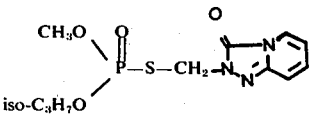

7. A compound according to claim 1 wherein such compound is 0-methyl-0-isopropyl-S-[3-oxo-triazolo-(4,3-α)-pyridin(2)ylmethyl]-thiolphosphoric acid ester of the formula

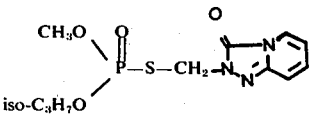

8. An insecticidal or acaricidal composition containing as active ingredient an insecticidally or acaricidally effective amount of a compound according to claim 1 in admixture with a conventional carrier.

9. A method of combating insect or acarid pests which comprises applying to the pests or a habitat thereof an insecticidally or acaricidally effective amount of a compound according to claim 1.

10. The method according to claim 9 wherein such compound is
0,0-dimethyl-S-[3-oxo-triazolo-(4,3-α)-pyridin-(2)ylmethyl]-thionothiolphosphoric acid ester,
0-ethyl-S-[3-oxo-triazolo-(4,3-α)-pyridin(2)ylmethyl]-methanethionothiolphosphonic acid ester,
0,0-dimethyl-S-[3-oxo-triazolo-(4,3-α)-pyridin-(2)ylmethyl]-thiolphosphoric acid ester,
0,0-diethyl -S-[3-oxo-triazolo-(4,3-α)-pyridin-(2)ylmethyl]-thiolphosphoric acid ester, or
0-methyl-0-isopropyl-S-[3-oxo-triazolo-(4,3-α)-pyridin(2)ylmethyl]-thiolphosphoric acid ester.

* * * * *